United States Patent [19]

Krause et al.

[11] Patent Number: 4,803,365
[45] Date of Patent: Feb. 7, 1989

[54] OPTICAL PROBE MOUNTING DEVICE

[75] Inventors: Richard J. Krause, Perkasie; Jaw F. Lee, Newtown Sq.; Craig W. Breckenridge, Allentown, all of Pa.

[73] Assignee: BioChem Technology, Malvern, Pa.

[21] Appl. No.: 47,850

[22] Filed: May 8, 1987

[51] Int. Cl.⁴ ............................................. G01N 21/64
[52] U.S. Cl. ............................ 250/461.2; 250/432 R; 250/461.1
[58] Field of Search ............. 250/461.2, 492.1, 432 R, 250/343, 357.1, 239, 461.1; 356/43, 44; 285/93

[56] References Cited

U.S. PATENT DOCUMENTS

| | | | |
|---|---|---|---|
| 2,397,901 | 4/1946 | Zimmerman | 356/44 |
| 4,189,236 | 2/1980 | Hogg et al. | 250/461.2 |
| 4,401,326 | 8/1983 | Blair | 285/93 |
| 4,573,761 | 3/1986 | McLachlan et al. | 356/301 |
| 4,577,110 | 3/1986 | MacBride et al. | 250/461.2 |
| 4,650,318 | 3/1987 | Pointer et al. | 356/43 |
| 4,654,532 | 3/1987 | Hirschfeld | 250/461.2 |
| 4,666,297 | 5/1987 | Suarez-Gonzalez | 356/43 |

FOREIGN PATENT DOCUMENTS

| | | | |
|---|---|---|---|
| 0017071 | 2/1977 | Japan | 356/43 |
| 0080729 | 5/1985 | Japan | 356/43 |
| WO87/04247 | 7/1987 | World Int. Prop. O. | 250/461.1 |

Primary Examiner—Janice A. Howell
Assistant Examiner—William F. Rauchholz
Attorney, Agent, or Firm—Austin R. Miller

[57] ABSTRACT

An optical probe mounting device for the insertion end of a fluorescence measuring optical probe which facilitates mounting on a biological reactor vessel window fitting. The device consists of a rigid hollow cylinder sized to closely receive the probe and to closely slide within the interior of the fitting. A quartz window seals the insertion end of the cylinder to allow passage of ultraviolet light without attenuation. A flange is sealingly affixed to the cylinder which permits the cylinder to extend a predetermined distance into the vessel. An O-ring extends around the cylinder or a face seal is used on the rear flange of the well, thereby providing a seal upon insertion of the device into the fitting.

5 Claims, 4 Drawing Sheets

OPTICAL PROBE MOUNTING DEVICE

BACKGROUND OF THE INVENTION

The present invention relates to a device for positioning an optical probe on a vessel, particularly to an optical well for a fluorescence optical probe to be mounted in a conventional access fitting on a biological reactor vessel.

FIELD OF THE INVENTION

Culture cell characteristics are often measured by illuminating a cell containing culture medium with selected wavelengths of light and detecting fluorescence emitted by the cells. Typically, such cells are contained in a biological reactor vessel. The vessels are conventionally outfitted with inlet and outlet lines, valves, gauges, windows, portals and the like. These allow for addition of gases, nutrients, stirring or agitation, measurement of pH or temperatures and measurement of fluorescence.

Manufacturers of such vessels typically provide fittings which are welded to the vessel. These fittings are eqipped with bolt holes, screw threads or the like in order that the above-mentioned gauges, valves, etc. be connected to the vessel. Vessel manufacturers have developed standard fittings which provide connections for these standard gauges, etc. For example, 19 mm and 25 mm fittings are well-known in the art. There has also been developed a so-called "Ingold" ® fitting which is known in the art.

DESCRIPTION OF THE Prior Art

Because many vessels and standardized vessel fittings are in common use, manufacturers of measuring apparatus design and construct measurement instruments suitable for use with these standard fittings. U.S. Pat. No. 4,577,110, to McBride et al, and assigned to BioChem Sensors, Inc. of Malvern, Pa, a company related to the assignee hereof, the disclosure of which is incorporated herein by reference, discloses such a fluorescence measuring instrument which may be employed using a standard "Ingold" fitting. The measuring system of that patent, utilizing the principle of fluorescent activation, has proved very effective, efficient and accurate.

Vessels of the type used in our aforesaid U.S. Pat. No. 4,577,110 are often steam sterilized in place or the vessel is autoclaved prior to innoculation to the culture medium already in the vessel. The fluorescence measuring device of the patent can be connected to the standard fitting if the medium has not first been introduced into the vessel. However, because the measuring instrument typically extends into the vessel (to obtain accurate measurements), it too must be sterilized. The measuring devices contain electronic parts and/or components which may not be exposed to moisture or high temperatures of autoclaving. Only portions extending into the vessel, which must be constructed to withstand such conditions, are sterilized during steam sterilization.

Inserting the probe after autoclaving would require the probe trip to be chemically or flame sterilized. Such a procedure must be undertaken for every probe, for example, that is to be employed for a given reaction. This is of course inconvenient and increases the chance of contamination. Another problem associated with current apparatus is that once a probe or gauge has been attached to a vessel, it must remain in place for the duration of the reaction. If it is moved or removed, the reactor vessel will leak or empty out, or at the least will be exposed to possible contamination from the atmosphere.

A further disadvantage connected with current apparatus is the lack of flexibility available. Fluorescence measuring apparatus tends to be quite expensive. In situations where many are being run simultaneously, separate probe and associated controls, read out devices, etc. are required for every reactor vessel, which can be prohibitive.

U.S. Pat. No. 4,189,236 to Hogg et al discloses a radiation collector apparatus for analyzing a flow of dilute particulate materials. A first tube introduces flow into a chamber while a second tube receives the flow after it has been illuminated. A laser beam or alternative radiant energy is applied to the flow through an entrance hole. The beam exits the chamber at an exit hole. The flow of material and the light beam are positioned so as to intersect, thereby creating reflected rays, which rays converge at a focus point positioned within an exit window. The exit window is shaped to receive a light detector, within a cavity. The cavity is substantially closed at one end except for a small hole.

This construction suffers from many of the disadvantages of current practices. Because the window is attached to the vessel, it lacks flexibility or interchangeability between vessels. It also restricts access to light flowing out from the vessel because of the pinhole orifice. Further, the window does not extend into the vessel so as to be able to make accurate measurements.

OBJECTS OF THE INVENTION

It is an object of the present invention to provide an optical probe mounting device for monitoring a fluorescence measuring optical probe to a standard window fitting on a biological reactor vessel.

It is another object of the present invention to provide an optical probe mounting device for mounting a fluorescence measuring optical probe on a biological reactor vessel which allows the probe to be mounted without sterilization, facilitates interchangeability of the probe between different reactor vessels and allows a detector to be removed for repair during fermentation.

It is yet another object of the present invention to provide an optical probe mounting device for mounting a fluorescence measuring optical probe on a biological reactor vessel which effectively seals against leakage or spillage and reduces exposure of vessel contents to harmful contamination, especially in the case of autoclavable vessels where the probe would be inserted after sterilization.

It is a still further object of the present invention to provide an optical probe mounting device for mounting a fluorescence measuring optical probe which allows probe generated ultraviolet light and cell emitted fluorescence to pass between a biological reactor vessel and probe without attenuation.

Other objects and advantages of the present invention will become apparent to those skilled in the art from the drawings, the detailed description of preferred embodiments and the appended claims.

SUMMARY OF THE INVENTION

An optical probe mounting device for the insertion end of a fluorescence measuring optical probe which facilitates mounting on a biological reactor vessel window fitting. The device consists of a rigid hollow cylinder sized to closely receive the probe and to closely slide within the interior of the fitting. A quartz window seals the insertion end of the cylinder to allow passage of ultraviolet light without attenuation. A flange is sealingly affixed to the cylinder which permits the cylinder to extend a predetermined distance into the vessel. An O-ring extends around the cylinder or a face seal is used on the rear flange of the well, thereby providing a seal upon insertion of the device into the fitting.

DETAILED DESCRIPTION OF THE DRAWINGS

Figure 1:
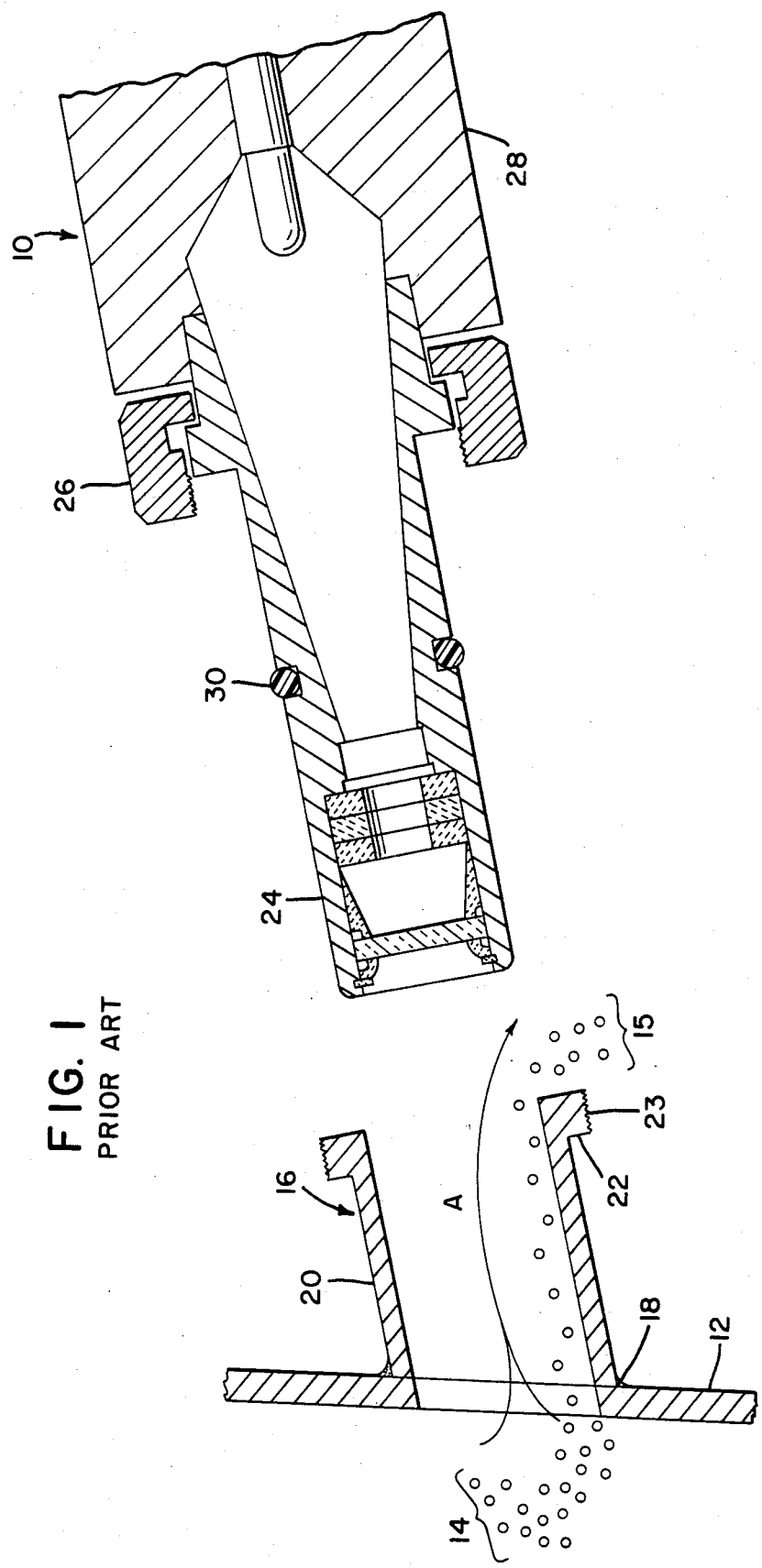
FIG. 1 is a transverse partial sectional view of a prior art device illustrating the optical probe depicted in FIG. 1 broken away and disconnected from the reactor vessel "Ingold" fitting.

FIG. 1 shows a fluorescence measuring optical probe 10 disengaged from wall 12 of a biological reactor vessel containing among other constitutents, a multiplicity of culture cells 14. In operation (not shown) probe 10 is specifically mounted to "Ingold" ® fitting 16. Fitting 16 is welded along weld 18 to wall 12 as a permanent fixture. Fitting 16 consists of a tube portion 20 and a threaded flange portion 22 with threads 23.

Probe 10 consists of an extension portion 24 extending directly into the vessel and closely engages cells 14. Extension 24 attaches to flange portion 22 by way of threaded ring nut 26. Body portion 28 of probe 10 connects to extension 24. O-ring 30 seals extension 24 along the tube portion 20 against leakage of vessel contents.

In FIG. 1, extension 24 of probe 10 is disengaged from tube portion 20 and ring nut 26 has been threadingly disengaged from flange portion 22. Cells 14 and culture medium within the reactor vessel are flowing outwardly in the direction of arrow A as cells 15.

Figure 2:
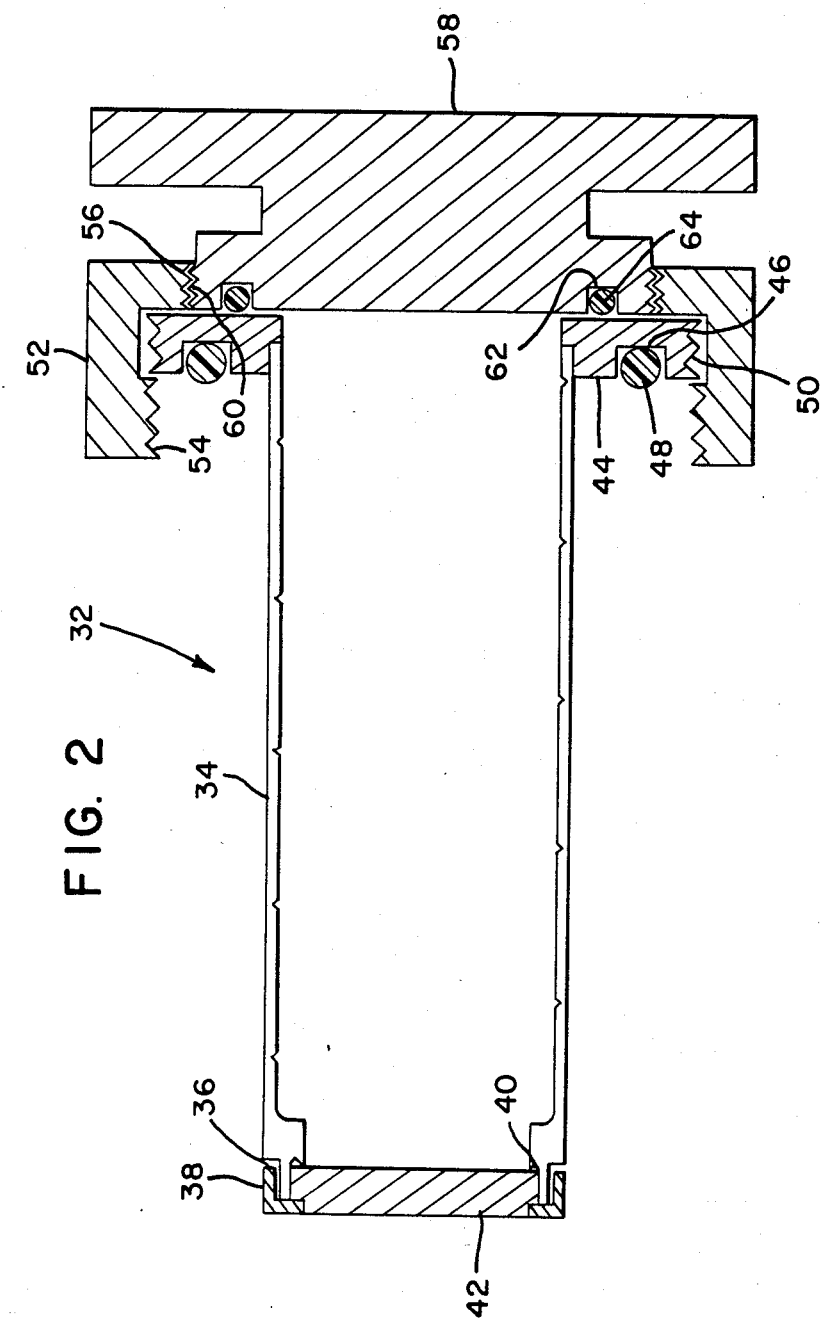
FIG. 2 is a transverse sectional view of an optical probe mounting device in accordance with aspects of the invention.

Referring to FIG. 2, a fluorescence measuring optical probe mounting device 32, hereinafter referred to as optical well 32, is shown. Cylindrically shaped tube 34 contains outer groove 36 into which optical well window cap 38 resides. Inner groove 40 receives quartz optical well window 42.

Optical well flange 44 is fixed to the opposite end of tube 34. Flange 44 contains slot 46 which houses flange O-ring 48. Flange 44 also has exteriorly facing threads 50. Optical well locking nut 52 rotatably surrounds flange 44. Locking nut 52 has interiorly facing attachment threads 54 and interiorly facing safety threads 56.

Optical well safety cap 58 removably engages safety threads 56 of locking nut 52 by way of exteriorly facing cap threads 60. Safety cap 58 contains slot 62 which houses safety cap O-ring 64.

Figure 3:
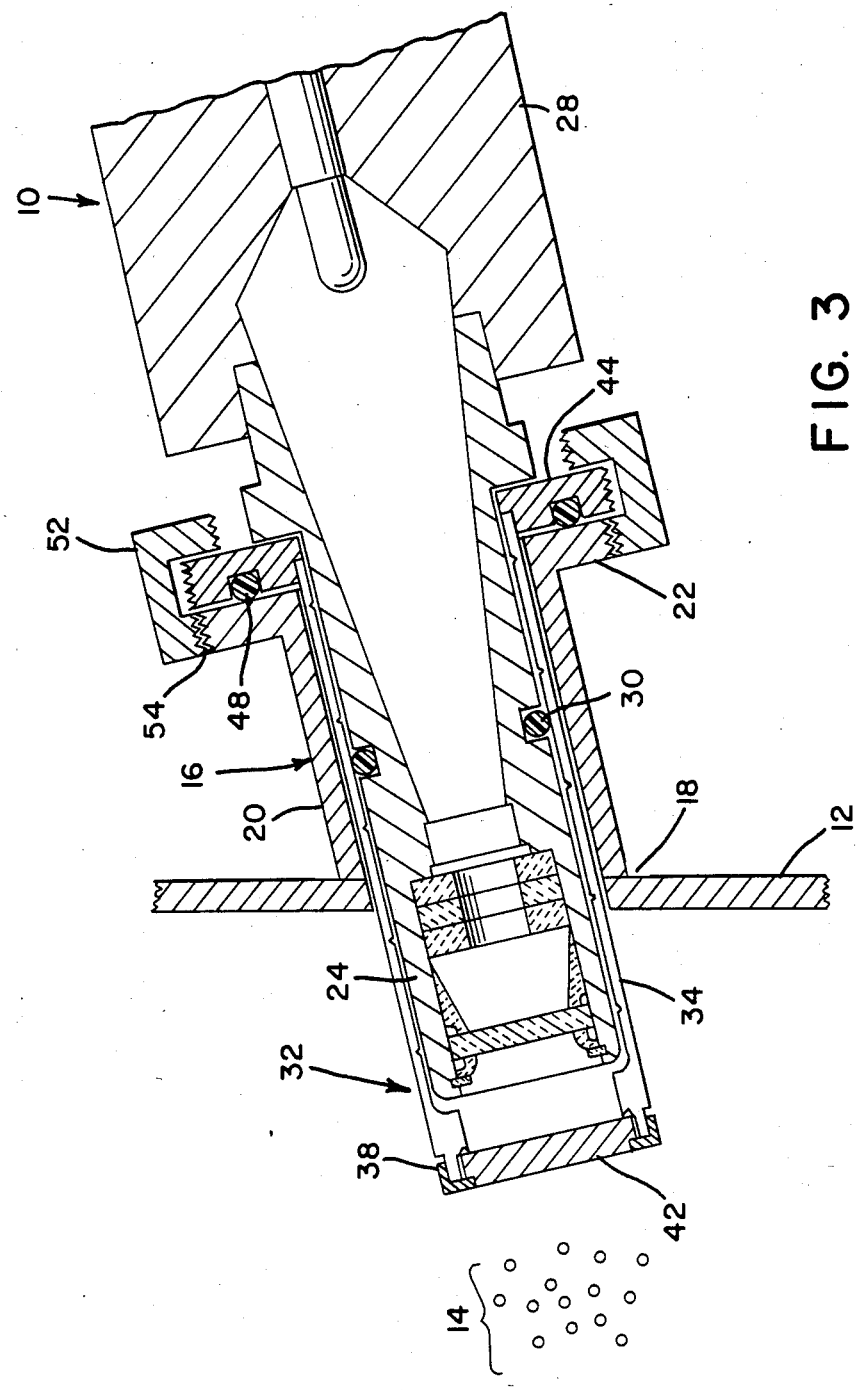
FIG. 3 shows a transverse partial sectional view illustrating an optical probe mounted in a conventionally outfitted reactor vessel employing an optical probe mounting device in accordance with the invention.

In FIG. 3 optical well 32 is sealingly mounted on fitting 16 and extends into the reactor vessel. Lock nut 52 engages flange portion 22 with attachment threads 54. O-ring 48 sealingly contacts flange portion 22.

Probe 10 is shown mounted into optical well 32 with extension 24 extending into and along tube 34. The extended end of extension 24 resides adjacent opitcal well window 42 so as to detect cell 14 emitted fluorescence.

Figure 4:
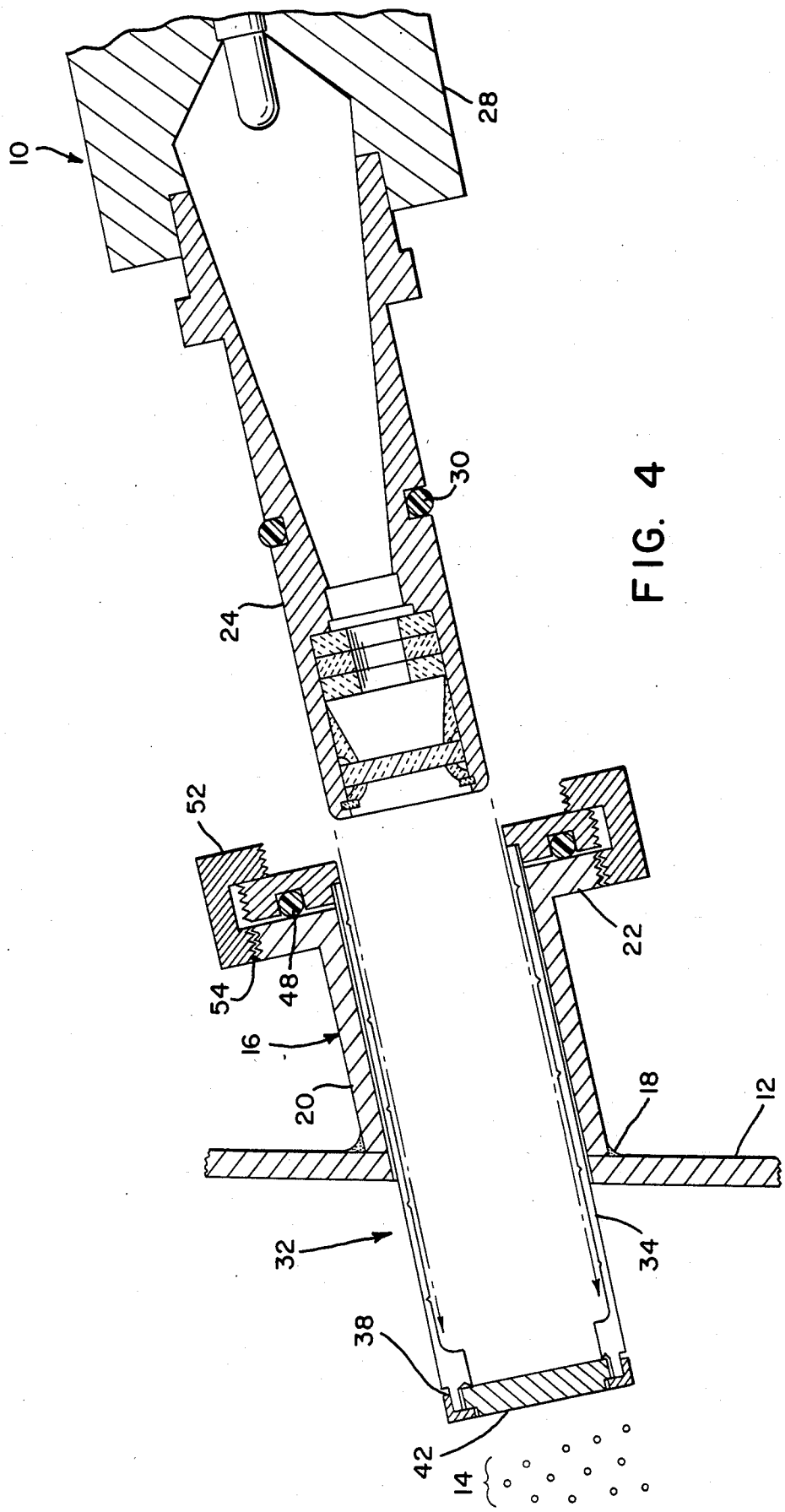
FIG. 4 is a transverse sectional view of the optical probe shown in FIG. 4 broken away from and disconnected from the optical probe mounting device of the invention.

FIG. 4 resembles FIG. 3 in that optical well 32 is mounted onto fitting 16. However, probe 10 no longer engages optical well 32. Extension 24 of probe 10 is free from engagement with tube 34. Optical well 32 remains sealingly attached to fitting 16 by way of attachment threads 54 of locking nut 52 engaging flange portion 22. O-ring 48 maintains the seal between fitting 16 and optical well 32.

Under current practice as shown in FIG. 1, probe 10 is directly mounted to fitting 16 in wall 12 for measuring emitted fluorescence of cells 14. However, prior to measuring fluorescence the subject reactor vessel must be equipped with the necessary measurement apparatus. Under prior art conditions the reactor vessel and any measuring apparatus, gauges, stirrers, etc, that will contact the cell medium must be completely sterilized. Since probe 10 should extend into the culture medium to obtain accurate fluorescence measurements, it too must be sterilized. However, such heat sterilizations are undesirable when autoclaving the complete vessel, since probe 10 contains delicate electronic and wire components. These components tend not to be suited to exposure to high sterilizing heat or moisture.

In the past probe 10 has been directly attached to fitting 16 and sealed into place by ring nut 26, and only then may the culture medium be introduced. After steam sterilization in place or autoclaving of all relevant parts, cells 14, innoculants, nutrients and the like may be added. However, after the reaction begins, probe 10 must remain attached to the vessel and in position. FIG. 1 shows probe 10 having been removed from fitting 16 during a reaction. Cells 14 in the vessel immediately are allowed to flow out of the vessel as cells 15 by way of open fitting 16. The problems associated with an open fitting 16 are apparent—cells 15 leak out and remaining cells 14 are immediately exposed to harmful contaminants.

Because of the impractical results brought about by removing probe 10, it must remain in position until the reaction is complete. This is undesirable because optical probes and their related equipment can be very expensive. In situations where multiple vessels are in use, it is highly desirable to have one probe which can measure fluorescence in several vessels in a short time.

Optical well 32 allows such flexibility. Before starting a reaction, optical well 32, which is preferably constructed of metal, quartz glass and a rubber seal, can be sterilized or autoclaved along with the reactor vessel without potential damage to delicate component parts. Optical well 32 is attached or mounted to fitting 16 by way of lock nut 52 prior to charging the vessel with culture medium, cells 14, etc.

To apply optical well 32, tube 34 is slid into tube portion 20 of fitting 16 until flange 44 contacts flange portion 22 of fitting 16. Lock nut 52 is then rotated to engage attachment threads 54 with theads 23 of flange portion 22. Lock nut 42 forces both flanges 22 and 44 tightly together and also allows rear flange O-ring 48 to sealingly engage flange 22.

At this point the reactor can be charged with reactants, even without probe 10 having been mounted. Optical well 32 provides a seal against leakage and contamination. Probe 10 is then mounted into optical well 32 whenever ready. Well 32 is provided with a quartz window 42 which allows passage of ultraviolet light without attenuation, which can be critical to probe accuracy. If it is desired to remove probe 10 for any purpose, such as to measure fluorescence in a nearby vessel, optical well allows such removal without leakage of reactor vessel contents, as is shown in FIG. 4.

If probe 10 must be removed for a comparatively lengty period of time, optical well 32 can be provided with an optional safety cap 58. Cap 58 effectively seals off the interior portion of well 32 against collecion of dust, rupture of the quartz window or against allowing exterior light into the vessel where multiple fluoresent probes are used in the vessel.

Optical well 32 is preferably constructed of stainless steel, although it is possible to utilize alternate materials. It is also preferred that O-rings 48 and 64 be employed as sealing means. It is however, possible that other seals positioned in alternate locations, such as on tube 34 for example, of optical well 16 be utilized to accomplish tight sealing against leakage of reactor vessel contents. Different seal constructions other than O-rings may be employed to achieve tight sealing. It is also possible to employ alternative types of glasses other than quartz glass in applications not involving ultraviolet light measurement. Further, optical well 32 may be mounted in fittings fixed to the top of a reactor vessel in addition to said mounting.

Although this invention has been described in connection with specific forms thereof, it will be appreciated that a wide array of equivalents may be substituted for the specific elements shown and described herin without departing from the spirit and scope of this invention as described in the appended claims.

I claim:

1. An optical well for receiving the insertion end of a removable fluorescence measuring optical probe facilitating mounting on a biological reactor vessel window fitting comprising:
   a rigid hollow cylinder extending within said vessel and sized to closely receive said removable probe to allow said probe to closely slide within the interior of said fitting;
   window means sealed to said cylinder at a location within said vessel and closing off the insertion end of said cylinder, said window means being constructed from quartz to allow passage of ultraviolet light without undue attenuation;
   a flange sealingly affixed to said cyliner outside said vessel and having a sealable surface positioned to contact said fitting to permit said cylinder to extend into said vessel a predetermined distance; and
   seal means extending along said sealable surface which sealingly contacts said fitting upon insertion of said well into said fitting to prevent leakage from said vessel along a path between said fitting and said well.

2. An optical well as defined in claim 1 wherein said seal means comprises an O-ring.

3. An optical well as defined in claim 1 wherein said well is constructed of stainless steel.

4. An optical well for receiving the insertion end of a removable fluorescence measuring optical probe facilitating mounting on a biological reactor vessel window fitting comprising:
   a rigid elongated hollow cylindrically shaped tube extending within said vessel and sized to closely receive said removable probe to allow said probe to closely fit within the interior of said fitting;
   window means sealingly capping the insertion end of said tube at a location within said vessel;
   a flange sealingly mounted on said tube outside said vessel and having a sealable surface, said flange acting to restrict said tube to extend into said vessel a predetermined distance; and
   seal means fixed along said sealable surface which sealingly contacts said fitting after insertion of said well into said fitting to prevent leakage from said vessel along a path between said fitting and said well.

5. A sleeve for mounting on a biological reactor vessel and capable of carrying a removable fluorescence measuring optical probe comprising:
   an elongated cylindrically shaped tube extending within said vessel and sized to slide within a portal fitting on said vessel;
   quartz window means sealing one end of said tube at a position within said vessel and capable of passing ultraviolet light therethrough without undue attenuation;
   lip means sealingly fixed to said cylindrical tube outside said vessel and having a sealable surface which contacts said fitting to permit said cylindrical tube to slide a prescribed distance into said vessel, said lip means having a central opening through which said removable probe passes into said cylindrical tube; and
   seal means extending along said lip means for contacting an end surface of said fitting to prevent leakage of contents of said vessel.

* * * * *